United States Patent [19]

Kronman et al.

[11] 4,121,587
[45] Oct. 24, 1978

[54] ROOT CANAL DELIVERY SYRINGE

[75] Inventors: Joseph H. Kronman, Canton; Melvin Goldman, Worcester, both of Mass.

[73] Assignee: National Patent Development Corporation, New York, N.Y.

[21] Appl. No.: 773,895

[22] Filed: Mar. 3, 1977

[51] Int. Cl.[2] .............................................. A61M 5/00
[52] U.S. Cl. ................................. 128/218 P; 128/236
[58] Field of Search ......... 128/218 R, 218 P, 218 PA, 128/215, 234, 236, 224

[56] References Cited

U.S. PATENT DOCUMENTS

| | | | |
|---|---|---|---|
| 546,073 | 9/1895 | Mix | 128/236 X |
| 781,283 | 1/1905 | Higgins | 128/236 X |
| 786,697 | 4/1905 | Wackenhuth | 128/218 P |
| 843,587 | 2/1907 | De Pew | 128/236 X |
| 1,217,630 | 2/1917 | Powers | 128/218 N |
| 1,751,139 | 3/1930 | Feinstein | 128/236 X |
| 3,672,369 | 6/1972 | Brown | 128/218 P |

FOREIGN PATENT DOCUMENTS 730,817  10/1932  France ........................ 128/236

*Primary Examiner*—John D. Yasko

[57] ABSTRACT

An improved syringe is provided for root canal applications comprising a generally cylindrical or polygonal hollow barrel threaded internally at its distal end and at its proximal end, and a plunger which is substantially coextensive in length with and is adapted to slide through the cylinder. The plunger is closed face at its distal end and is externally threaded at its proximal end for threaded engagement with the internal threads at the proximal end of the cylinder. The plunger is integrally capped at its proximal end and the cap is provided with a handle for turning the plunger in order to insert it in or retract it from the cylinder. A needle is integrally attached to a hub which is provided with a central externally threaded tubular member adapted to threadedly engage with the internal threads of the distal end of the cylinder.

4 Claims, 4 Drawing Figures

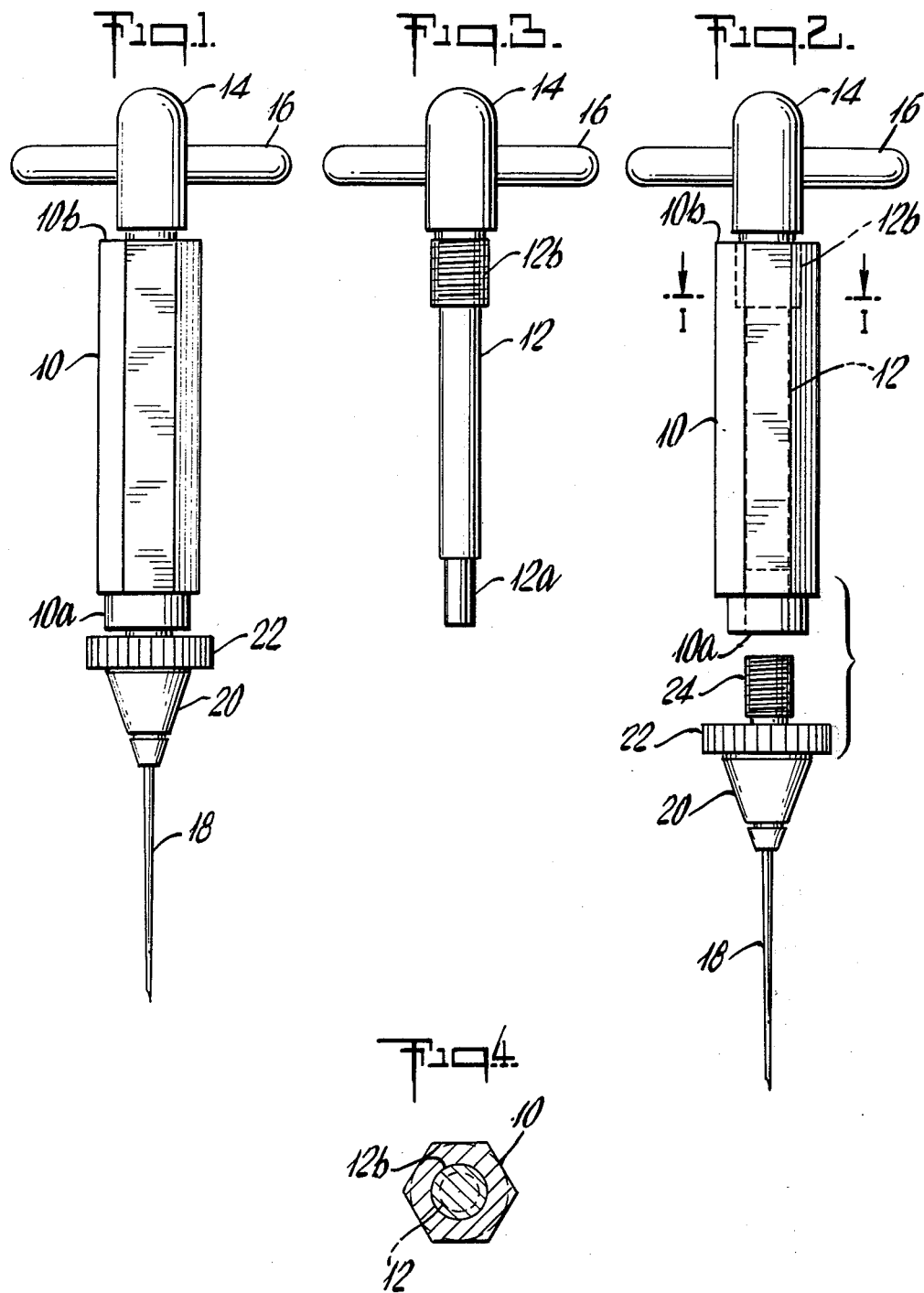

ROOT CANAL DELIVERY SYRINGE

FIELD OF INVENTION

This invention relates to syringes for root canal applications, and is particularly related to an improved syringe which is capable of more efficient delivery of root canal filling materials into the teeth cavities.

BACKGROUND OF INVENTION

Root canal therapy may involve the injection of a root canal filling material into the teeth cavities by means of a so-called pressure syringe which forces the filling material into said cavities. Other methods involve placement of solid gutta-percha and/or silver points coated with cement for filling the cavities, but these materials are difficult to apply and they do not completely penetrate into the fine crevices in the teeth cavities and, therefore, they frequently give poor filling performance. A more effective root canal filling material is described in U.S. Pat. No. 3,925,895 which issued on Dec. 16, 1975 and which is assigned to the assignee of the present application. The root canal therapy disclosed in said patent contemplates the injection into the tooth cavity of a hydrophyllic monomer (e.g., hydroxyethyl methacrylate) together with a suitable catalyst and an accelerator, and the in situ polymerization of said monomer in the tooth cavity. The monomer, catalyst and accelerator are mixed in a syringe to at least a paste-like consistency and then forced from the syringe into the root canal.

The root canal filling material described in said patent is more effective than the conventional root canal materials since it becomes hydrated and swells, thus filling and sealing the entire voids and crevices in the root canal.

A pressure syringe is available for root canal work which is not entirely satisfactory for injection of root canal filling materials such as the materials described in the aforementioned patent. Leakage of the material, inadequate obturation of the canal and loss of the filling material are but few of the disadvantages of the pressure syringe. Such pressure syringes are described by M. Greinberg in "Filling Root Canals of Deciduous Teeth by an Injection Technique," Dent. Digest 67: 574(December 1961) and in "Filling Root Canals by an Injection Technique," Dent. Digest 69: 61(February 1963). Accordingly, there is a need for a syringe which is suitable for the injection of root canal filling material of the type described in the aforementioned patent without the disadvantages and limitations which are inherent in the present pressure syringe system.

SUMMARY OF INVENTION

In accordance with the invention, the syringe comprises a generally cylindrical or polygonal hollow body having an internally threaded distal end and an internally threaded proximal end, and a plunger which is substantially coextensive in length with and is adapted to slide through said cylinder. The plunger is closed at its distal end and is partially threaded at its proximal end for threaded engagement with the proximal end of said cylinder.

At its proximal end, the plunger is integrally capped and the cap is provided with a handle for turning the plunger in order to insert the plunger in or retract it from the hollow cylinder.

A needle integrally attached to a hub is attached to the distal end of said cylinder as will hereinafter be described in further detail.

BRIEF DESCRIPTION OF THE DRAWINGS

FIG. 1 is a vertical elevational view of a syringe constructed in accordance with the principles of this invention;

FIG. 2 is a vertical elevational view of the syringe shown in FIG. 1, with parts broken away;

FIG. 3 is a vertical elevational view of the plunger and its integral handle, with the proximal end being threaded in accordance with this invention; and FIG. 4 is a top view of the syringe barrel taken along the line I—I of FIG. 1.

Like numerals are employed in the drawings to designate like parts.

DESCRIPTION OF THE PREFERRED EMBODIMENT OF THE INVENTION

Referring to the drawings, there is shown a generally cylindrical or polygonal (e.g. hexagonal) hollow body or barrel 10 which is partially threaded interiorly (not shown) at its distal end 10a as well as at its proximal end 10b. The term "distal end" refers to the end away from the syringe handle while the term "proximal end" refers to the end which is close to the syringe handle.

The syringe also comprises a plunger 12 which is substantially coextensive with and is adapted to slide through the axial bore in the hollow cylinder 10, although the plunger 12 may be slightly longer than the cylinder barrel, if desired. The plunger 12 is closed face at its reduced distal end 12a and is partially threaded at its proximal end 12b as shown in FIG. 3. The provision of a threaded portion at the proximal end of the plunger rather than at the distal end, as is common in other types of syringes, including the prior art pressure syringes, is one of the unique features of this invention as will hereinafter be explained in further detail.

At its proximal end 12b, the plunger 12 is provided with an integral cap 14 and handle 16 which serve to rotatably insert the plunger 12 into the cylinder 10 or to retract it therefrom. Thus, when the plunger 12 is inserted in the cylinder 10 and the handle 16 is turned clockwise until it can no longer be turned, the distal end 12a of the plunger is flush with the distal end 10a of the cylinder 10. In order to retract the plunger 12 from the cylinder barrel, handle 16 is simply turned counterclockwise.

The syringe system of this invention also comprises a needle 18 integral to a skirt 20 and a hub-like member 22. An externally threaded tubular member 24 integral with said hub-like member 22 is adapted to threadably engage with the internal threads of the distal end 10a of the cylinder 10.

In using the syringe of this invention for root canal therapy the filling material is placed in the hub 22 and the hub is then screwed onto the distal end of the barrel 10 as is shown in FIG. 1. Next, the plunger 12 is inserted into the barrel 10 and the handle 16 is turned clockwise thereby causing the reduced end 12a of the plunger 12 to be inserted into the tubular member 24. Continual turning of the handle 16 in the clockwise direction forces the filling material from the hub 22 into the needle 18 and out of the needle 18 into the tooth cavity.

If additional filling material is needed for the therapy, the plunger 12 is retracted from the barrel 10 by turning the handle 16 in a counterclockwise direction until the plunger is completely disengaged from the barrel. More filling material is then placed in the hub 22 and the root canal therapy repeated as hereinbefore described.

Contrary to the syringe system which is described herein, the relationship of the syringe barrel and the hub in the prior art type pressure syringe is such that there is intimate contact at their interface. Consequently, when the needle is wedged in the canal back pressure in the system causes leakage of the filling material and diminishes the ability of the syringe to completely obturate the canal with the filling material. Additionally, and contrary to the system described herein, there is no intimate contact between the plunger and the filling material in the prior art type pressure syringe due to the presence of an air cushion downstream of the plunger. This causes discontinuous injection of the filling material into the tooth cavity and hence poor performances by the prior art type pressure syringe.

As it was previously mentioned, the plunger of the syringe system of this invention is threaded at its proximal end in contradistinction from the plunger of the prior art type pressure syringe which is only threaded at its distal end. This difference is particularly significant when the filling material employed in root canal therapy is a paste-like material such as the material described in the aforementioned patent. It has been found that when the hub of the prior art type pressure syringe is filled with such paste-like filling material, turning the plunger causes some of the material to back up into the syringe barrel, whereas no significant back-flow of material is noticed when using the syringe described herein in which the plunger is threaded at its proximal end as aforesaid. Moreover, the provision of a plunger with a threaded proximal end as hereinbefore described insures smooth and substantially uniform flow of the root canal material from the syringe and into the root canal.

While the syringe system of this invention has heretofore been described in detail with certain degrees of particularities, it is understood, of course, that several modifications and changes can be made in its construction which are nevertheless within the scope of this invention and obvious from the description herein. For example, while in the description of the preferred embodiment of this invention, the distal end 12a of the plunger 12 is described as a threaded connection for engagement with the external threads of tubular member 24 (FIG. 2), the distal end connection may be of snap fit, bayonet mount or of any other suitable construction, in which case the distal end 12a of the plunger 12, the distal end 10a of the cylinder barrel and the tubular member 24 need not be threaded.

Also, the syringe system of this invention may be fabricated from metal or plastic, although metallic construction is preferable. It may be generally cylindrical, or polygonal in cross section such as the hexagonal configuration shown in FIG. 4, so long as it defines a substantially cylindrical hollow channel conformal with the plunger.

Thus, in accordance with this invention, a syringe is provided which is uniquely suitable for more effective root canal therapy using paste-like filling materials and particularly materials such as those described in the aforementioned patent.

What is claimed is:

1. A syringe which comprises, in combination, an elongated hollow body having interiorly threaded proximal end; a plunger which is at least substantially coextensive in length with said elongated hollow body and is adapted to slide therethrough, said plunger having a reduced distal end and an exteriorly threaded proximal end for threaded engagement with the interiorly threaded proximal end of said elongated hollow body, means secured to the proximal end of said plunger for rotatably turning said plunger into said elongated body; a hub-like member containing root canal filling material, said hub-like member having an externally threaded central tubular extension adapted to threadedly engage with the interiorly threaded distal end of said plunger, and an integral, generally frusto-conical hollow member, and a needle rigidly secured to said frusto-conical member.

2. A syringe as in claim 1 wherein said plunger is substantially coextensive in length with said elongated hollow body.

3. A syringe as in claim 1 wherein said means secured to said proximal end of said plunger is an end cap with integral handle.

4. A syringe as in claim 2 wherein said means secured to said proximal end of said plunger is an end cap with integral handle.

* * * * *